United States Patent [19]

Kühlein et al.

[11] 4,071,530

[45] Jan. 31, 1978

[54] PYRROLIDONES AND PROCESS FOR PREPARING THEM

[75] Inventors: Klaus Kühlein, Kelkheim, Taunus; Dieter-Bernd Reuschling, Butzbach; Milos Babej, Frankfurt am Main; Wilhelm Bartmann, Neuenhain, Taunus; Gerhard Beck, Frankfurt am Main, all of Germany

[73] Assignee: Hoechst Aktiengesellschaft, Frankfurt am Main, Germany

[21] Appl. No.: 628,479

[22] Filed: Nov. 4, 1975

[30] Foreign Application Priority Data

Nov. 6, 1974 Germany .............................. 2452536
June 24, 1975 Germany .............................. 2528036

[51] Int. Cl.² .......................................... C07D 207/26

[52] U.S. Cl. ................................ 260/326.45; 424/274
[58] Field of Search .................. 260/326.45, 326.5 FL

[56] References Cited

PUBLICATIONS

Ambrus et al, "Chem. Abstracts", vol. 84, (1976) Abst. No. 59286k.

*Primary Examiner*—Alton D. Rollins
*Assistant Examiner*—D. B. Springer
*Attorney, Agent, or Firm*—Curtis, Morris & Safford

[57] ABSTRACT

The present invention relates to pyrrolidone derivatives which are analogous to natural prostaglandins and to a process for preparing the same. The compounds according to the present invention have prostaglandin-like properties and may be used as pharmaceuticals.

4 Claims, No Drawings

PYRROLIDONES AND PROCESS FOR PREPARING THEM

The natural prostaglandins have a hydrocarbon skeleton of generally 20 carbon atoms. They are distinguished from one another by the number of the hydroxyl groups and double bonds. Since they simultaneously deploy a large number of physiological activities and have only a short half-life period in the organism, their use as therapeutic agents is limited.

Therefore, the search for prostaglandins having a longer half-life period and a specific activity is becoming more and and more important.

The present invention relates to novel pyrrolidones of the formula I

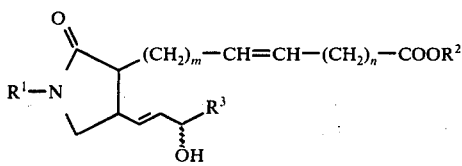

wherein the symbols have the following meanings: $R^1$ is a straight-chained or branched alkyl radical having 1 to 6 carbon atoms or a cycloalkyl radical having 3 to 7 ring members, whereby the cycloalkyl radical may be substituted by straight-chained or branched $(C_1-C_4)$-alkyl- or-alkoxy groups, $R^2$ is a straight-chained or branched $(C_1-C_4)$-alkyl radical, $R^3$ is a straight-chained or branched alkyl radical having 1 to 10 carbon atoms which may be substituted by an O- or S-alkyl radical having 1 to 5 carbon atoms, by a phenoxy radical which may be substituted by one or more alkyl groups having 1 to 3 carbon atoms which, for their part may contain halogen atoms, or the aforesaid phenoxy radical may be substituted by halogen atoms or optionally halogen-substituted phenoxy radicals, or $R_3$ is the aforesaid alkyl radical which may be substituted by an O-furyl radical or an O-benzyl radical, which for their part, may contain alkyl groups having 1 to 3 carbon atoms as substituents, or by a trifluoromethyl radical or a cycloalkyl radical having 3 to 7 ring members or a phenyl or furyl radical, which, for their part, may be substituted by one or several alkyl groups having 1 to 3 carbon atoms, and $m$ is identical to 1 to 2 and $n$ may be 2 or 3, and wherein the side chains in 3- and 4-position of the pyrrolidone ring are in a trans-position to each other, as well as the free acids of these compounds and the physiologically compatible metal or amine salts thereof.

The present invention further relates to a process for the preparation of pyrrolidones of the formula 1, wherein a. a pyrrolidone of the formula

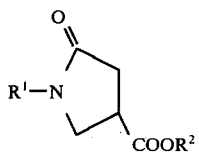

wherein $R^1$ and $R^2$ have the meaning of formula I, is reduced to a compound of the formula III

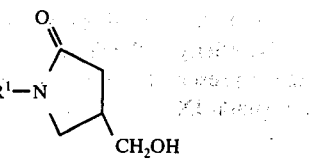

b. the alcohol function in a compound of the formula III is protected with a group easily split off under acidic conditions, whereby a compound of the formula IV

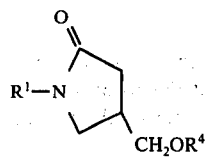

wherein $R^1$ has the meaning given in formula I and $R^4$ is a protective group which can be easily split off $c_1$. the ether of the formula IV, in the presence of a base of the formula V Me-B           V wherein Me is an alkali metal atom and B stands for hydrogen, a straight-chained or branched $(C_1-C_4)$-alkoxy radical or the group

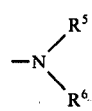

wherein $R^5$ and $R^6$ are identical of different and represent $(C_1-C_6)$-alkyl or $(C_3-C_6)$-cycloalkyl, is converted with an alkenyl halide of the formula $CH_2=CH-(CH_2)_m$-Hal, with $m = 1$ or 2, into an unsaturated compound of the formula VI

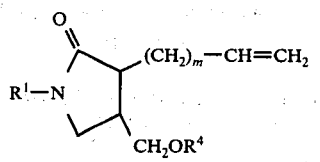

wherein $R^1$ and $m$ have the meaning given for the formula I and $R^4$ the meaning given for the formula IV, $d_1$. the compound obtained of the formula VI is subjected to an ozonolysis, whereby an aldehyde of the formula VII

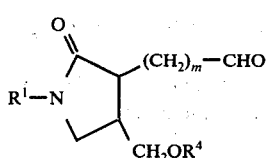

wherein $R^1$ and $m$ have the meaning given for the formula I and $R^4$ the meaning given for the formula VI, is formed, $e_1$. the aldehyde obtained of the formula VII is reacted with the ylide of the formula VIII

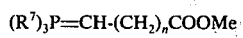

$(R^7)_3P=CH-(CH_2)_n COOMe$      VIII wherein $R^7$ means identical or different, straight-chained ($C_1$-$C_4$)-alkyl or phenyl radicals, Me is an alkali metal atom, and $n$ may represent the numbers 2 and 3, to a compound of the formula IX

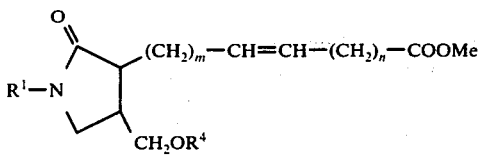
IX wherein $R^1$, $R^4$, $m$ and $n$ have the above meanings, $f_1$. the compound obtained of the formula IX is converted into the corresponding ester of the formula X

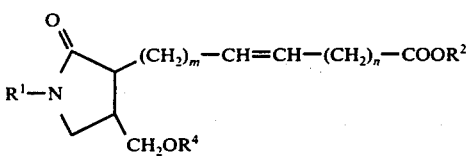
X wherein $R^1$, $R^2$, $m$ and $n$ have the meaning given for the formula I and $R^4$ has the above meaning, $g_1$. the protective group $R^4$ in a compound of the formula X is split off under acidic conditions, whereby an alcohol of the formula XI

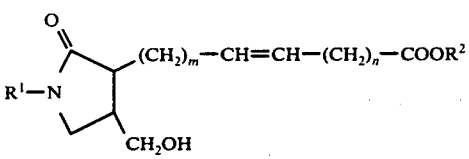
XI wherein $R^1$, $R^2$, $m$ and $n$ have the meaning given in formula I, is formed, or $g_1'$. the esterification of a compound of the formula IX as well as the splitting of the protective group $R^4$ is carried out in one step, $h_1$. the alcohol obtained of the formula XI is oxidized, whereby an aldehyde of the formula XII

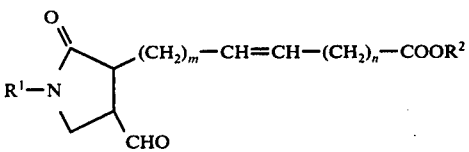
XII wherein $R^1$, $R^2$, $m$ and $n$ have the meaning given in formula I is obtained, $i_1$. the aldehyde obtained of the formula XII is reacted with a phosphonate of the formula XIII

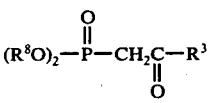
XIII wherein $R^3$ has the meaning given in formula I, and $R^8$ is a straight-chained ($C_1$-$C_4$)-alkyl radical, whereby a compound of the formula XIV

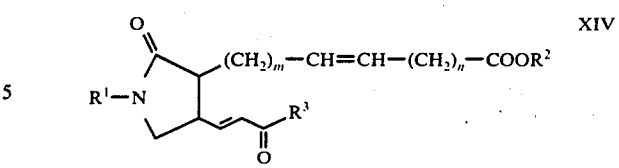
XIV is obtained, wherein $R^1$, $R^2$, $m$ and $n$ have the meaning mentioned in formula I, $k_1$. in the compound obtained of the formula XIV the cetone carbonyl is reduced whereby a compound of the formula I is obtained, and this compound is optionally converted into the free acid or the physiologically tolerable metal or amine or $c_2$. the ether of the formula IV is reacted in the presence of a base of the formula V

Me - B    V wherein Me and B are defined as above, with an alkyl halide of the formula XV

$Hal^1$—$(CH_2)_m$-C ≡ C—$(CH_2)_n$-$Hal^2$    XV wherein either $Hal^1$ stands for bromine and $Hal^2$ for chlorine or $Hal^1$ stands for iodine and $Hal^2$ for bromine or $Hal^1$ stands for iodine and $Hal^2$ for chlorine and $m$ and $n$ are defined as in formula I, to give a compound of the formula

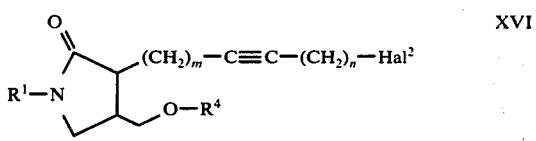
XVI $d_2$. the compound obtained of the formula XVI is reacted with an alkali metal cyanide, whereupon the cyanalkine of the formula XVII

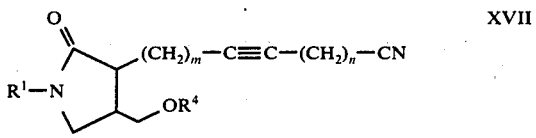
XVII wherein $R^1$, $m$ and $n$ are defined as in formula I and $R^4$ is defined as in formula IV, is obtained, $e_2$. the nitrile obtained of the formula XVII is hydrolized in a basic medium to give a compound of the formula XVIII

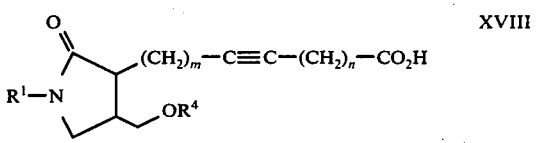
XVIII wherein $R^1$, $m$ and $n$ are defined as in formula I and $R^4$ is defined as in formula IV, $f_2$. the compound obtained of the formula XVIII is converted into an ester of the formula

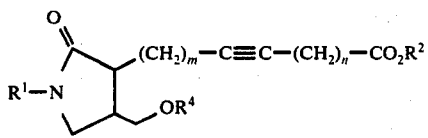

$$\text{XIX}$$

wherein $R^1$, $R^2$ $m$ and $n$ are defined as in formula I and $R^4$ is defined as in the formula IV, g$_2$. the protective group $R^4$ is split off in a compound of the formula XIX under acid conditions which gives an alcohol of the formula

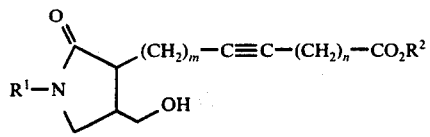

$$\text{XX}$$

wherein $R^1$, $R^2$, $m$ and $n$ are defined as in the formula I or f$_2'$. the esterification of the compound of the formula XVIII and the splitting off the protective group $R^4$ are carried out in a single operational step or e$_2'$. the nitrile group in the compound of the formula XVII is converted in the acid medium directly into the ester group while splitting off the protective group $R^4$ at the same time, h$_2$. the compound obtained of the formula XX is hydrogenated to a compound of the formula

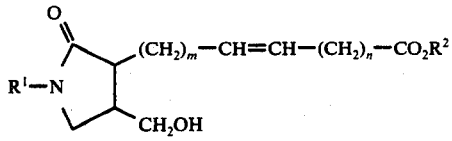

$$\text{XI}$$

wherein $R^1$, $R^2$, $m$ and $n$ are defined as in the formula I, and the process is continued according to the operational steps indicated in h$_1$) to k$_1$).

Among the meanings mentioned for $R_1$ there are preferred straight-chained alkyl radicals having 1 to 4 carbon atoms, the isopropyl radical as well as the tertiary butyl radical, cycloalkyl radicals having 5 to 6 ring members which may be substituted by straight-chained ($C_1$-$C_3$)-alkyl or-alkoxy groups, especially the cyclohexyl and the cyclohexyl methyl radical; among the meanings mentioned for $R^2$ there are preferred $C_1$-$C_4$ alkyl radicals, among the meanings given for $R^3$, alkyl radicals having 3 to 8 carbon atoms, cycloalkyl radicals having 5 to 7 carbon atoms as well as the phenyl radical or a phenyl radical substituted by one or more methyl groups. Further preferred groups for $R^3$ are radicals of the formula —C(R')$_2$—CH$_2$—O-R'', wherein R' represents ($C_1$-$C_3$)-alkyl radicals with the proviso that the two R' may be different from each other, and wherein R'' is a ($C_1$-$C_5$)- alkyl radical, a phenyl radical which may be substituted by one or more ($C_1$-$C_3$)-alkyl radicals, or a benzyl radical, which may be substituted by one or several ($C_1$-$C_3$)-alkyl radicals.

The pyrrolidones of the formula II used as starting compounds in the process of the invention and having a carboxyl group in 4-position may be obtained from itaconic acid or the esters thereof and primary amines. [P. L. Paytash, E. Sparrow and J. C. Gathe, J. Am. Chem. Soc. 72, 1415 (1950); R. Anschutz and F. Reuter, Ann. 254, 129 (1889),] O. Scharfenberg, Ann. 254, 149 (1889). The reactions starting from the itaconic acid are preferably carried out in an aqueous solution at temperatures between 100° and 200° C. But the reactions with the itaconic acid esters are preferably carried out in organic solvents such as diethyl ether, tetrahydrofuran, methylene chloride or benzene at 0°–80° C. In the first case, 4-hydroxycarbonyl-pyrrolidones are obtained which, for the first process step, must be converted into the esters according to one of the usual methods. In the second case the esters required are obtained directly.

The process of the invention begins with converting the 4-alkoxycarbonyl-pyrrolidones of the formula II into the 4-hydroxymethyl-pyrrolidones of the formula III, which is possible by catalytic hydrogenation as well as with complex metal hydrides.

As catalysts for the hydrogenation there may be used numerous metals and precious metals as for example Raney-Nickel, copper chromium oxide and ruthenium oxide on charcoal. The hydrogenations are all carried out at 100°–250° C, preferably at 140°–180° C and 150–250 atmospheres gauge in a suitable solvent.

As solvents there are preferably used alcohols such as methanol, ethanol or isopropanol or ethers such as tetrahydrofurane and dioxane. The development of the reduction is observed by thin layer chromatography (CHCl$_3$:C$_2$H$_5$OH = 95:5). Double bonds in the molecule are also saturated under these hydrogenation conditions.

The reduction with complex metal hydrides is preferably carried out with LiBH$_4$ in ethers such as diethyl ether, dioxane or THF at temperatures between 0° and 80° C, preferably at 20°–60° C with exclusion of moisture in an inert gas atmosphere.

To isolate the hydroxymethyl compounds, the catalyst is filtered or the metal hydride in excess is destroyed by addition of 2N sulfuric acid, the solvent is removed and the remaining residue is mixed with a sufficient amount of benzene to remove water traces and concentrated again. The distillation residue is then subjected to a fractionated high vacuum distillation.

As protective groups for the hydroxymethylpyrrolidones, there are considered above all those which may be split off again under mild reaction conditions, for example by acidic hydrolysis or by hydrogenation. Especially the allyl-, benzyl, tert.-butyl- and chloromethyl radical as well as enol ether groups comply with this condition [E. J. Corey, J. W. Suggs, J. Org. Chem. 38, 3224 (1973); E. J. Corey, P. A. Grieco, Tetrah. Lett. 107 (1972)].

The formation of acetals is preferred. These may be prepared by reacting the alcohols of the formula (III) with enol ethers, as for example dihydropyrane, in an aprotic solvent in the presence of a catalytic amount of a strong acid. As acids there may be used mineral acids, as for example hydrochloric acid or sulfuric acid, or phosphorus oxychloride, or organic acids, as for example p-toluene-sulfonic acid or trifluoroacetic acid.

Halogen hydrocarbons such as chloroform, methylene chloride or nitriles, as for example acetonitrile, have proved advantageous as solvents. The reaction is preferably carried out at 0° to 20° C. The reaction times may amount from one hour to about 24 hours. To isolate the compounds of the formula IV the reaction mixture is shaken with a sufficient amount of an acid acceptor, preferably with saturated sodium bicarbonate solution, the organic phase is dried with sodium sulfate and the product is purified after removing the solvent by high vacuum distillation or column chromatography. In the next process step the compounds (IV) are deprotonized to the carbonyl group in α-position with a suitable base and then reacted with an alkenyl halide, preferably alkyl bromide, or 4-bromo-butene (1) to obtain a product of the formula VI.

The bases of the formula (V) are known in the literature. Me means in (V) an alkali metal; lithium, sodium or potassium are preferred. If B means the radical

$R^5$ and $R^6$ are straight-chained or branched ($C_1$–$C_6$)-alkyl radicals as for example methyl, ethyl, propyl, pentyl, hexyl, preferably isopropyl or in the case of a ($C_3$–$C_6$)-cycloalkyl group example cyclopropyl, cyclobutyl, cyclopentyl, especially cyclohexyl.

Especially preferred as compounds of the formula (V) are sodium hydride, potassium-tert.-butylate, lithium diisopropyl amide and lithium-cyclohexyl-isopropylamide.

Due to the sensitivity of the bases of air and humidity and the resulting carbon ions the reaction of the base (V) with the compounds of the formula (IV) is carried out with the exclusion of air and humidity. As solvents there are considered especially aprotic polar solvents which also in the case of low temperatures have a sufficient solubilizing capacity and are inert under the reaction conditions. If desired, mixtures of two or several solvents are used to reduce the solidification point. There are preferred for example ethers, as for example dimethyl ether, diethyl ether, diisopropyl ether, tetrahydrofurane, glycol dimethyl ether, furthermore dimethyl formamide, dimethyl sulfoxide or toluene. The amounts of the solvents have to be measured in such a way as to obtain in each case homogeneous solutions.

The reaction temperatures are between −100° C and +10° C, preferably between −80° and −20° C, especially between −70° C and −40° C. The reaction is generally carried out in the following way: while stirring, a solution of the pyrrolidone of the formula (IV) is added to a deeply-cooled solution of the base (V) in one of the solvents mentioned, so that the temperature range desired for the reaction is maintained. The combination of the components may also take place in reverse order. The deprotonization of the pyrrolidone is generally finished after about 30 minutes.

Subsequently the alkenyl halide is added to the deeply-cooled solution thus obtained, so that the temperature range of the reaction mixture is not considerably exceeded by the exothermic reaction.

After that, stirring is continued for half an hour to 12 hours at low temperature, the mixture is slowly heated to room temperature and worked up.

Working up can occur in the following way: the reaction mixture is mixed with a certain amount of water, the organic phase is separated, dried and concentrated. The residue may be purified in some cases by high vacuum distillation, in most cases by column chromatography. However, the products are often obtained in a pure state, so that purification is not necessary.

The conversion of the olefins of the formula VI into the aldehydes of the formula VII by ozonolysis is effected in analogy to the literature [P. S. Bailey, Chem. Rev. 58, 990 (1958), J. J. Pappas, W. P. Keaveney, E. Gancher, M. Berger, Tetrah. Lett. 36, 4273 (1966)] in the following way:

The olefins are dissolved with exclusion of humidity in a certain amount of absolute methanol to which a halogen hydrocarbon, as for example methylene chloride, is optionally mixed. At temperatures between −100° C and −50° C, preferably −70° C, the equivalent amount of ozone is introduced into these solutions. A small excess of ozone does not have any influence on the yield. Subsequently the ozone in excess is expelled by an inert gas, for the reduction of the ozonolysis products dimethyl sulfide is added, and stirring is continued for about one hour at −10° C, 0° C and 20° C in each case.

To isolate the aldehydes the solutions are evaporated in vacuo at temperatures as low as possible, the residue is treated with saturated sodium bicarbonate solution and then the product is extracted with a suitable solvent, preferably benzene.

The aldehydes are used either directly or after previous purification, for example by column chromatography, for the subsequent Wittig reaction.

The compounds of the formula IX are obtained by reaction of a phosphonium ylide of the formula VIII, wherein the radical $R^7$ preferably means phenyl, with the aldehydes of the formula VII in a suitable solvent. The phosphonium ylides and the phosphonium salts from which they derive are prepared according to analogous prescriptions described in the literature. [i.e. E. J. Corey, N. M. Weinschenker, T. K. Schaaf, W. Huber, J. Amer. Chem. Soc. 91, 5675 (1969)].

For the preparation of the ylide there may be used inorganic bases such as sodium hydride, sodium amide, lithium amide or potassium-tert.-butylate or organic bases, as for example alkali metal organic compounds, as for example lithium butyl, lithium diisopropyl amide or the sodium salt of dimethyl sulfoxide.

As solvents there are suitable ethers as for example diethyl ether, tetrahydrofurane, diethylene glycol dimethyl ether, di-lower-alkyl sulfoxides such as dimethyl sulfoxide or amides of carboxylic acids as for example dimethylformamide, dimethylacetamide and others.

The solvent preferred is dimethyl sulfoxide. As a base there is preferably used the sodium salt of dimethyl sulfoxide, because under these conditions cis-double bonds are preferably formed.

The preparation of the ylide and the introduction of the upper side chain is effected in a one pot reaction.

The details of the reaction proceed as follows:

The solution of the phosphonium salt is added at room temperature, with exclusion of humidity and under inert gas, to an equivalent of a base which is also dissolved in an aprotic solvent, for example dimethyl sulfoxide. After stirring for about one hour a solution of 0.75 to 0.95 equivalent of the aldehyde is added. The reaction is finished after 2 - 24 hours. The solution is acidified with a mineral acid at −5° to +5° C, the acid is extracted from the reaction mixture with a suitable solvent as for example ether, methylene chloride or benzene, the organic base is dried and concentrated. To separate by-products and the phosphine oxide, the acid is converted again into the alkali metal salt thereof and the aqueous phase is extracted with a suitable solvent.

From the aqueous phase the free carboxylic acids of the compounds of the formula IX are isolated by acidifying and extracting again with a suitable solvent.

The esters of the formula X or XI may be prepared according to analogous processes described in the literature. Thus, for example the acids may be esterified with the corresponding alcohol in the presence of a strong acid such as sulfuric acid, hydrochloric acid, p-toluene-sulfonic acid, trifluoro-acetic acid and other acids, if desired in the presence of a entraining agent for the water formed. The alcohol is used in excess.

Under these conditions the protective group $R^4$ is simultaneously split off and the compounds of the formula XI are obtained directly.

But in the esterification with alcohols in the presence of carbodiimides, the protective group $R^4$ is not affected. The reaction with diazo alkanes, preferably diazo methane, in an inert solvent leads to the same result.

As far as the carboxylic acids used for esterification have not been purified, a chromatographic purification on the stage of the esters XI is recommended.

The splitting off of the protective group $R^4$ and the esterification may be carried out in one step, as described above. Otherwise, the esters of the formula X are heated for about 30 minutes to 50°–80° C for splitting off the protective group, in the presence of acidic catalysts in an alcohol such as methanol, ethanol or isopropanol. Then the whole is neutralized and the compound of the formula XI is isolated by extraction with a suitable solvent, as for example methylene chloride, chloroform of diethyl ether.

As in the operational step ($c_2$), the compounds of the formula IV are deprotonized with a base of the formula Me-B in the α-position and subsequently reacted with an alkinyldihalide, for example 1-iodo-6-bromo-hexine-(2) or, preferably, 1-bromo-6-chloro-hexine-(2) in analogy to the operational step ($c_1$), the same reaction conditions being maintained as in the operation step described under $c_1$). The alkinyl dihalides of the formula XV can be prepared according to A. J. Rachlin, N. Wasyliw and M. W. Goldberg, J. Org. Chem. 26, 2688 (1961).

The nitriles of the formula XVII are prepared by dissolving an alkali metal cyanide in a mixture of solvents, for example ethanol/water, dimethylformamide/water or preferably in pure dimethyl sulfoxide and adding the halogen compound of the formula XVI dropwise, after its dissolution in the same solvent, at 60°–120° C, especially between 80° C and 90° C to the alkali metal cyanide solution. After the addition was completed, the mixture was stirred for 2–8 hours at 80°–90° C. The nitriles of the formula XVII are isolated for example in such a manner that a determined amount of water is added to the reaction mixture and it is extracted with an organic solvent not miscible with water. The products are obtained in such a pure state that they can be used without further purification for the next reaction steps. The alkaline hydrolysis of the nitriles of the formula XVII to the carboxylic acid of the formula XVIII is effected according to methods described in the literature (cf., for example Autorenkollektiv: "Organikum", VEB Deutscher Verlag der Wissenschaften, Berlin 1967, page 411). For example a solution of the nitrile is heated for 10–20 hours to 80° C, with twice the molar amount of an aqueous 25% strength sodium hydroxide solution in an amount of ethanol sufficient for a homogeneous solution. Then, the mixture was acidified with a mineral acid and the free carboxylic acid was extracted with an organic solvent which is not miscible with water.

The esters of the formula XIX or XX can be prepared according to processes described in the literature. For example the acids can be esterified with the corresponding alcohol in the presence of a strong acid, such as sulfuric acid, hydrochloric acid, p-toluenesulfonic acid, trifluoroacetic acid and others, if necessary in the presence of an entrainer for the water formed. The alcohol is used in excess in this operation.

Under these conditions the protective group $R^4$ is split off simultaneously and the compounds having the formula XX are directly obtained.

However, in the esterification with alcohols in the presence of carbodiimides, the protective group $R^4$ is not attacked. The reaction with diazo alkanes, preferably diazo methane, in an inert solvent leads to the same result.

If the carboxylic acids used for the esterification have not been purified it is recommended to purify by chromatography during the formation of the esters XX.

The splitting off of the protective group $R^4$ and the esterification can be carried out in a single step operation as described above. If not, the esters of the formula XIX can be heated to 50° C–80° C for about 30 minutes to split off the protective group in the presence of acid catalysts in an alcohol, for example methanol, ethanol or isopropanol, preferably $R^2OH$. Then, they are neutralized and the compound of the formula XX is isolated by extracting with a suitable solvent, for example methylene chloride, chloroform or diethylether.

The esters of the formula XX are obtained directly from the nitrile of the formula XVII when they are dissolved in an excess of an alcohol, the solution is saturated at 5° to −20° C, preferably 0° to −5° C with dry hydrogen chloride and after about 2 to 4 hours the solvent and the excess hydrogen chloride are carefully eliminated under reduced pressure, taken up in alcohol again, the pH is adjusted to 1 to 4, preferably to 1–2 with 33% strength aqueous alkali metal hydroxide solution and the mixture is then heated to 60°–80° C for 0.5 to 3 hours. The esters of the formula XX are isolated for example by the elimination of the solvent and following extraction of the residue with an organic solvent. It is recommended to purify the ester subsequently by chromatography.

The stereoselective partial hydrogenation of the compounds of the formula XX to the compounds of the formula XI having a cis-double bond can be carried out according to known methods (cf. H. C. Brown: Hydroboration, W. A. Benjamin Inc., New York 1962; Houben-Weyl: Methoden der organischen Chemie, Georg Thieme Verlag, Stuttgart 1970, vol. XIII/4, pages 135–141; ibid. vol. V/1 b, 1972, page 585 et seq.).

Catalytic hydrogenation at room temperature with palladium catalysts having a reduced catalytic effect, especially with palladium on calcium carbonate (10% Pd) in the presence of quinoline, is preferred. Suitable solvents are methanol, ethanol, glacial acetic acid and ethyl acetate, preferably, however, benzene.

For the isolation, the catalyst is filtered off and the filtrate is worked up in usual manner, for example by distilling off the solvent.

The oxidation of the compounds of the formula XI to the compounds of the formula XII is effected with oxidation agents usual for the oxidation of aliphatic alcohols to aldehydes.

Some methods are described in Houben-Weyl, volume 7/1, page 159. Further suitable oxidating agents are the complexes formed from thio ethers such as dimethyl sulfides or thioanisole with chlorine or N-chloro-succinimide [E. J. Corey, C. U. Kim, J. Amer. Chem. Soc. 94, 7586 (1972), E. J. Corey, C. U. Kim, J. Org. Chem. 38, 1233 (1973)].

Furthermore the oxidation with dimethyl sulfoxide may be applied under very different conditions [W. W. Epstein, F. W. Sweat, Chem. Rev. 67, 247 (1967)].

A particularly preferred process is the oxidation with the chromium trioxide pyridine complex. The complex is first prepared in an inert solvent, preferably methylene chloride, and at $-10°$ to $+10°$ C a solution of the alcohol XI is added. The oxidation proceeds quickly and is usually finished after 5 to 30 minutes.

The aldehyde of the formula XII may be used without further purification for the next process step. If desired the aldehyde is purified by column chromatography.

The reaction of the phosphonates of the formula XIII with compounds of the formula XII may be carried out under the conditions usual for the Horner reaction, for example in ethers at room temperature. As ethers there are preferred diethyl ether, tetrahydrofurane and dimethoxy-ethane. To complete the reaction the phosphonate is used in excess. The reaction is usually finished after one to five hours at room temperature. The reaction product is then isolated by usual processes from the reaction mixture and purified by column chromatography.

The phosphonates of the formula XIII are either known [D. H. Wadsworth et al. J. Org. Chem. 30, 680 (1965)] or may be prepared in analogy to known processes.

Compounds of the formula I may be obtained by treating the compounds of the formula XIV with a reducing agent. The reduction may be carried out with reducing agents which render possible a selective reduction of a keto group to a hydroxyl group. Preferred reducing agents are complex metal hydrides, especially the boron hydrides such as sodium boron hydride, zinc boron hydride or lithium perhydro-9$b$-boraphenalkyl-hydride [H. C. Brown, W. C. Dickason, J. Amer. Chem. Soc. 92, 709 (1970)]. The reduction is usually carried out between 0° and 50° C in a solvent inert with regard to the hydrides as for example diethyl ethers, dimethoxy ethane, dioxane, tetrahydrofurane or diethylene glycol dimethyl ether. The isomeric $\alpha$ - and $\beta$-hydroxy compounds resulting from this reduction may be separated into the two isomers with the aid of the usual methods as for example thick layer or column chromatography. Their conversion into the free acids is effected by one of the usual saponification methods. The preparation of pharmacologically suitable salts from the acids is effected in the usual manner. The acid is dissolved in a solvent such as water, methanol, tetrahydrofurane, neutralized with the corresponding organic or inorganic base and if the salt is not precipitated, a solvent having a suitable polarity is added such as methanol, ethanol, dioxane, or the solution is evaporated until dry.

From the organic bases, the alkali metal or alkaline earth metal hydoxides are preferred. Among the organic bases those are considered which derived from primary, secondary and tertiary amines, as for example methyl, dimethyl, trimethyl, phenylethyl amine, ethylene diamine, allyl amine, piperidine, morpholine and pyrrolidine. Amines containing hydrophilic groups, as for example ethanol amine and ephedrine, are considered. As quaternary bases there are considered for example tetramethyl and benzyltrimethyl ammonium hydroxide.

The esters of the formula (I), the acids from which they derive and the salts which may be easily prepared therefrom show effects similar to prostaglandins. The novel compounds have luteolytic properties, properties inhibiting the secretion of gastric juice, bronchospasmolytic and/or antihypertensive properties. Furthermore, the novel compounds of the invention are also useful and valuable as intermediate products for the preparation of other substances having a prostaglandin effect.

The compounds of the formula III, IV, VI, VII, IX, X, XI, XII, XIV, XVI, XVII, XVIII, XIX, and XX are novel intermediate products for the preparation of the compounds of the formula I.

Acids and salts or esters can be used in the form of their aqueous solution or suspension or also as solutions in pharmacologically tolerable organic solvents, for example, mono- or multivalent alcohols and their glycerol esters, in dimethylsulfoxide or dimethyl formamide, but also in the presence of pharmacologically tolerable polymer carriers, for example polyvinyl pyrrolidone.

Preparations may be infusion or injection solutions as well as aerosols, tablets and capsules.

For administration in aerosol form, the compounds of the invention may be dissolved in the usual physiologically tolerated solvents which are not irritating with regard to taste, for example water or ethanol, or suspended, for example in lower alkyl esters of higher fatty acids, for example myristic acid isopropyl ester, if desired with the addition of surface-active agents as stabilizers, for example sorbitane- or pentaerythritol fatty acid ester, and filled, together with one of the usual inert propellant gases, in aerosol containers. However, the aforementioned compositions may also be administered by means of a conventional atomizer with the aid of compressed air.

The following dosage units and daily doses, determined with guinea pigs (broncho dilating effect) and dogs (blood-pressure-lowering effect), respectively, may be administered for the various possible indications:

| Bronchodilating action (as aerosol) | |
|---|---|
| Dosage unit: | 0.1 – 1000 µg |
| preferred: | 1 – 200 µg (per single spray output) |
| Daily dose: | 0.1 – 10 mg |
| Blood-pressure - lowering action: | |
| Dosage unit: | 1 – 1000 µg |
| preferred: | 1 – 100 µg parenterally (i.v.) |
| Daily dose: | 1 – 10 mg |
| Dosage unit: | 0.5 – 10,000 µg |
| preferred: | 1   5,000 µg orally |
| Daily dose: | 1 –   10 mg |

The doses administered for gastro-intestinal disorders correspond to those indicated for administration as blood-pressure-lowering agents.

EXAMPLES

A. Preparation of the starting compounds:

1. 4-Carbomethoxy-1-isopropyl-pyrrolidone (II)

In the course of 30 minutes, 59.1 g (1 mol) of isopropyl amine were added dropwise to 158 g (1 mol) of itaconic acid methyl ester in 120 ml of diethyl ether.

When the slightly exothermic reaction had finished, the reaction mixture was allowed to stand for 24 hours at room temperature. Then the solvent was removed in vacuo and the residue was subjected to fractionated vacuum distillation. boiling point: 95–98° C/0.05 mm Hg; $n_D^{20}$: 1.4680

In analogy there were obtained:

1.1: 1-Tert.-butyl-4-carbomethoxy-pyrrolidone after reflux for 24 hours of the ethereal solution boiling point: 103° – 105° C: 0.05 mm Hg 1.2: 4-Carbonmethoxy-1-methyl-pyrrolidone in analogy to Example (1)
boiling point: 105° C/0.5 mm Hg; $n_D^{20}$: 1.4752

1.3: 1-Benzyl-4-carbomethoxy-pyrrolidone in analogy to Example (1.1) melting point: 163° C 1.4: 1-n-butyl-4-carbomethoxy-pyrrolidone in analogy to Example (1) boiling point: 125° – 127° C/0.05 mm Hg: $n_D^{20}$: 1.4680

B. Examples of the process:

2. 4-Hydroxymethyl-1-isopropyl-pyrrolidone (III)

92.5 g (0.5 mol) of 4-carbomethoxy-1-isopropyl-pyrrolidone in 1.2 l of ethanol were hydrogenated in the presence of about 50 g of Raney-Nickel for 48 hours at 160° – 180° C under a hydrogen pressure of 200 atmospheres. Then it was determined with the aid of thin layer chromatography ($CHCl_3/C_2H_5OH$= 95:5) if the reduction was finished. Otherwise 20 g of Raney-Nickel were added again and hydrogenated for another 24 hours. In most of the tests hydrogenation had finished after this time.

The catalyst was filtered with exclusion of air, the filtrate was concentrated in vacuo, the residue was mixed with 500ml of benzene and concentrated again. The product was then distilled over a Vigreux column having a 30 cm length. boiling point: 152° C/0.08 mm Hg; melting point: 45° C.

2.1: 1-tert.-butyl-4-hydroxymethyl-pyrrolidone

In analogy to Example (2) Melting point: 64° – 65° C.

2.2: 4-Hydroxymethyl-1-methyl-pyrrolidone

Instead of Raney-Nickel, hydrogenation was carried out with 10 g of ruthenium on charcoal (5 %) for 6 days at 150° C and a hydrogen pressure of 150 – 200 atmospheres. boiling point: 150° – 160° C/ 17 mm Hg; $n_D^{20}$: 1.4948

2.3: 4-Hydroxymethyl-1-methyl-pyrrolidone

A solution of 2.3g (106 m moles) of $LiBH_4$ in 150 ml of diethyl ether was slowly added dropwise at +5° C to 17.0g (107 m mols) of 4-carbomethoxy-1-methyl-pyrrolidone in 20 ml of absolute diethyl ether. Stirring was continued for 2 hours at room temperature, then the mixture was acidified with 2N sulfuric acid ($p_H$ 2), the solvent and water were distilled off to a large extent in vacuo and the remaining residue was extracted with methylene chloride. The dried methylene chloride phase was concentrated and the residue was distilled in vacuo. 5 g of the compounds desired were obtained in a 98% purity: $n_D^{20}$: 1.4950.

2.4: 1-Cyclohexylmethyl-4-hydroxymethyl-pyrrolidone in analogy to Example (2)
Melting point: 82° C 2.5: 1-n-Butyl-4-hydroxymethyl-pyrrolidone in analogy to Example (2)
boiling point: 143°–147° C/ 0.05 mm Hg; $n_D^{20}$: 1.4800

3.
1-Methyl-4-(2-tetrahydropyranyl-oxy-methyl)-pyrrolidone (IV)

6 drops of concentrated hydrochloric acid and 4 drops of water were added to a mixture of 73 g (565 m mols) of 4-hydroxymethyl-1-methyl-pyrrolidone and 142 g (1.7 mol) of dihydropyrane in 200 ml of methylene chloride while stirring. After a short time an exothermic reaction began. By occasional cooling with ice the reaction temperature was maintained between 15° and 25° C. With the aid of thin layer chromatography ($CHCL_3/C_2H_5OH$ = 95:5) the end of the reaction was observed, which was the case after about 4 hours. 50 ml of saturated sodium bicarbonate solution were added while stirring, the organic phase was subsequently separated, the aqueous phase was extracted three times with 200 ml in each case of methylene chloride, the combined methylene chloride phases were dried and evaporated in vacuo. The remaining residue was fractionated in vacuo.

The desired compound was obtained as a colorless liquid having a boiling point of 128° C/0.05 mm Hg; $n_D^{20}$: 1.4858; $R_f$: 0.23 (ethyl acetate).

3.1:
1-n-Butyl-4-(2-tetrahydropyranyl-oxy-methyl)-pyrrolidone

Corresponding to Example (3)
The purification is effected in this case by column chromatography (silica gel/ethyl acetate); $n_D^{20}$: 1.4812; $R_f$ = 0.32 (ethyl acetate)

3.2:
1-Cyclohexylmethyl-4-(2-tetrahydropyranyl-oxy-methyl)-pyrrolidone

Corresponding to Example (3)
$R_f$ = 0.49 (ethyl acetate); $n_D^{20}$: 1.4945

4.
3-Allyl-1-methyl-4-(2-tetrahydropyranyl-oxy-methyl)-pyrrolidone (VI)

20.0 g of 1-methyl-4-(2-tetrahydropyranyl-oxy-methyl)-pyrrolidone (94 mmols) dissolved in 100 ml of diethyl ether were added, while stirring, at −70° C, to 0.1 mol of $Li(NiC_3H_7)_2$ in 100 ml of diethyl ether. After stirring for one hour at −70° C, 19.4 g of allylbromide (160 mmols) were added dropwise. The mixture was slowly heated to room temperature, 50 ml of water were added dropwise, the organic phase was separated, the aqueous phase was extracted three times with 100 ml in each case of methylene chloride, the combined organic phases were dried with sodium sulfate and concentrated in vacuo. A slightly yellow oil remained. [$n_D^{20}$ : 1.4891; $R_f$ : 0.44 (ethyl acetate)]After column chromatograhy ($SiO_2$/ethyl acetate) the above compound was obtained as a colorless oil ($n_D^{20}$: 1.4888).

4.1:
3-Allyl-1-n-butyl-4-(2-tetrahydropyranyl-oxy-methyl)-pyrrolidone

In analogy to Example (4) $n_D^{20}$: 1.4852; $R_f = 0.72$ (ethyl acetate)

4.2:
3-(Butenyl)-1-methyl-4-(2-tetrahydropyranyl)-oxy-methyl)-pyrrolidone 10.6 g (50 mmols) of 1-methyl-4-tetrahydropyranyl-oxymethyl)-pyrrolidone were deprotonized according to Example (4) at −70° C with 53 mmols of LiN(iC$_3$H$_7$)$_2$ and subsequently mixed with 6.7 g of 4-bromobutene (1) in 10 ml of diethyl ether. The mixture was heated within 16 hours to room temperature, mixed with 50 ml of water, the pH value was adjusted to 7 by addition of diluted hydrochloric acid and the reaction product was isolated as described in Example (4). 10.5 g of crude product were obtained. [$n_D^{20}$: 1.4819; $R_f= 0.70$ (ethyl acetate) ]By column chromatography (SiO$_2$/ethyl acetate) the product may be freed from slight contaminations.

5.
3-Formylmethyl-1-methyl-4-(2-tetrahydropyranyl-oxy-methyl)-pyrrolidone (VII)

20.4 g of 3-allyl-1-methyl-4-(2-tetrahydropyranyl-oxy-methyl)-pyrrolidone (80 mmols were dissolved in a mixture of 65 ml of absolute methylene chloride and 30 ml of absolute methanol cooled to −70° C and treated with ozone until the solution had a visible blue color. Ozone in excess was removed at −70° C by introducing a dry nitrogen stream. 16 ml of dimethyl sulfide were added dropwise, the whole was stirred for 30 minutes at −70° C and subsequently for one hour in each case at −10° C, 0° C and room temperature.

The reaction solution was concentrated in vacuo at a bath temperature of a maximum of 40° C; the residue was mixed with 20 ml of saturated sodium bicarbonate solution and the aqueous phase was extracted four times with 100ml of benzene in each case. The benzene phase was dried over sodium sulfate and evaporated in vacuo under mild conditions. 20.2 g of the aldehyde were obtained. $R_f = 0.24$ (ethyl acetate); $n_D^{20}$: 1.4920 Contaminations may be separated by column chromatography (SiO$_2$/ ethyl acetate)

5.1:
1-n-butyl-3-formaldehyde-4-(2-tetrahydropyranyl-oxy-methyl)-pyrrolidone in analogy to Example (5) $R_f = 0.51$ (ethyl acetate); $n_D^{20}$: 1.4888

5.2:
3-Formylethyl-1-methyl-4-(2-tetrahydropyranyl-oxy-methyl)-pyrrolidone 11.0 g (41 m mols) of 3-(butenyl)-1-methyl-4-(2-tetrahydropyranyl-oxy-methyl)-pyrrolidone were dissolved in a mixture of 60 ml of absolute methyle chloride and 30 ml of absolute methanol. At −70° C ozone was introduced into this solution, while stirring, until the solution had a blue color. The reduction of the ozonide with dimethyl sulfide and the isolation of the aldehyde was effected in analogy to Example (5).

The crude product (15.0) was purified by column chromatography (silica gel/ethyl acetate). $R_f = 0.28$ (ethyl acetate); $n_D^{20}$: 1.4808

6.
1-Methyl-3-[6′-hydroxy-carbonyl-(Z)-2′-hexen-yl-(1′)]-4-(2-tetrahydropyranyl-oxy-methyl)-pyrrolidone (IX)

A suspension of 9.0 g of sodium hydride (375 m mols) in 125 ml of absolute dimethyl sulfoxide was heated to 60°–70° C until the development of hydrogen had finished. The mixture was cooled to 15° C and a solution of 81.6 g of 5-triphenyl-phosphonio-pentanoic acid bromide (188 m mols) in 200 ml of dimethyl sulfoxide were added while cooling with ice, stirring was continued for one hour at 20° C and a solution of 47.0 g of 3-formyl-methyl-1-methyl-4-(2-tetrahydropyranyl-oxy-methyl)-pyrrolidone (184 mmols) in 50 ml of absolute DMSO was added dropwise, at 15° C. After stirring for 3 – 15 hours at 15° C, 200 ml of 2N H$_2$SO$_4$ were added dropwise at about 10° C, then 100 ml of saturated NaCl solution were added and extracted five times with 500 ml of benzene in each case.

The benzene phases were dried over sodium sulfate and evaporated in vacuo. The oily residue of 181.0 g was vigorously shaken with a mixture of 150 ml of saturated sodium bicarbonate solution and 7.0 g of sodium bicarbonate. The aqueous phase was separated, extracted twice with 200 ml of ethyl acetate in each case, cooled to about −15° C and while stirring about 100 ml of 2N sulfuric acid were added ($p_H = 1$).

The mixture was saturated with sodium chloride and extracted immediately five times with 500 ml of methylene chloride in each case.

The residue was purified by column chromatography (SiO$_2$/ethyl acetate).

Rf = 0.66 (CHCl$_3$/C$_2$H$_5$OH = 9:1); IR CHCl$_3$) :ν=1725 (C═O); 1795 (C═O)cm$^{-1}$

6.1:
2-N-butyl-3-[6′-carbohydroxy-(Z)-2′-hexene-yl(1′)]-4-(2-tetrahydropyranyl-oxy-methyl)-pyrrolidone In analogy to Example (6) from 1-N-butyl-3-formyl-methyl-4-(2-tetrahydropyranyl-oxy-methyl)-pyrrolidone and the ylide of the 5-triphenyl-phosphonio-pentanoic acid Rf = 0.76 (CHCl$_3$/C$_2$H$_5$OH = 9 : 1); IR (CHCl$_3$):ν = 1725 (C═O); 1795 (C═O)cm$^{-1}$

6.2:
1-Methyl-3-[6′-carbohydroxy-(Z)-3′-hexene-yl(1′)]-4-(2-tetrahydropyranyl-oxy-methyl)-pyrrolidone In analogy to Example (6) from 3-formylethyl-1-methyl-4-(2-tetrahydropyranyl -oxy-methyl)-pyrrolidone and the ylide from 4-triphenylphosphonio-butyric acid.

Rf = 0.66; IR (CHCl$_3$) :ν=1725 (C═O); 1795 (C═O) cm$^{-1}$

7.
1-Methyl-3-[6′-carbomethoxy-(Z)-2′-hexene-yl(1′)]-4-(2-tetrahydropyranyl-oxy-methyl)-pyrrolidone (X)

To 5.0 g (14.5 mmols) of 1-methyl-3-[6′-carbohydroxy-(Z)-2′-hexene-yl (1′)] -4-(2-tetrahydropyranyl-oxy-methyl)-pyrrolidone in 100 ml of methylene chloride 40 ml of a 0.5 molar ethereal diazo-methane solution were added at 0° C. Within one hour the solution was heated to room temperature and concentrated in vacuo. The desired compound was obtained as a colorless oil.

Rf = 0.44 (ethyl acetate); IR (CHCl$_3$):ν = 1680 (C═O); 1740 ( C ═ O ) cm$^{-1}$

7.1:
1-Methyl-3-[6'-carbomethoxy-(Z)-3'-hexen-yl-(1')]-4-(2-tetrahydropyranyl-oxy-methyl)-pyrrolidone In analogy to Example (7) from 1-methyl-3-[6'-carbohydroxy-(Z)-2'-hexen-yl(1')] -4-(2-tetrahydropyranyl-oxy-methyl)-pyrrolidone and ethereal diszomethane solution.

Rf = 0.44 (ethyl acetate); IR (CHCl$_3$):$\nu$ = 1680 (C=O); 1740 (C=O)cm$^{-1}$

8.
1-Methyl-3-[6'-carbomethoxy-(Z)-2'-hexen-yl(1')]-4-hydroxy-methyl-pyrrolidone (XI)

A one molar methanolic solution of 14.1 g (40 mmols) of 1-methyl-3-[6'-carbomethoxy-(Z)-2'-hexen-yl(1')]-4-(2-tetrahydropyranyl-oxymethyl)-pyrrolidone was mixed with five drops of concentrated hydrochloric acid and refluxed for a short time. Then the solvent was removed in vacuo, 5 ml of saturated sodium bicarbonate solution were added to the residue and the above compound was isolated by extracting three times with 50 ml of methylene chloride in each case. When evaporating the dried organic phase, the alcohol remained as a thick colorles oil.

Rf= 0.31 (CHCl$_3$/C$_2$H$_5$OH=9,5/0,5); IR(CH$_2$Cl$_2$):$\nu$=1680 (C=O); 1740 (C=O); 3450 (OH) cm$^{-1}$

8.1:
1-N-Butyl-3-[6'-carbomethoxy-(Z)-2'-hexene-yl(1')]-hydroxymethyl-pyrrolidone A solution of 15.2 g (40 mmols) of 1-N-butyl-3-[6'-carbomethoxy-(Z)-2'-hexene-yl(1')]-4-hydroxymethyl-pyrrolidone in 30 ml of absolute methanol and 100 ml of benzene was refluxed for 10 hours. The solvent was removed in vacuo, the residue was taken up in 40 ml of methanol and refluxed for a short time with addition of five drops of concentrated hydrochloric acid. Then the mixture was worked up as described in Example (8). The alcohol was obtained as a colorless oil. Rf = 0,43 (ethyl acetate); IR (CH$_2$Cl$_2$):$\nu$= 1680 (C=O); 1740 (C=O); 3450 (OH) cm$^{-1}$

8.2:
1Methyl-3-[6'-carbomethoxy-(Z)-3'-hexene-yl(1')]-4-hydroxy-methyl-pyrrolidone in analogy to Example (8)
Rf = 0.32 (CHCl$_3$/C$_2$H$_2$OH = 9,5 : 0,5); IR (CH$_2$Cl$_2$):$\nu$=1680 (C=O); 1740 (C=O); 3450 (OH) cm$^{-1}$

9.
1-Methyl-3-[6'-carbomethoxy-(Z)-2'-hexene-yl(1')]-4-formyl-pyrrolidone (XII)

Into a stirred solution of 15.8 g (200 mmols) of pyridine in 240 ml of methylene chloride, 10.0 g (100 mmols) of chromium trioxide were introduced portionwise at room temperature. Stirring was continued for 20 minutes at room temperature, the mixture was cooled to 0° C and a solution of 3.23 g (12 mmols) of 1-methyl-3-[6'-carbomethoxy-(Z)-2'-hexen-yl(1')]-4-hydroxy-methyl-pyrrolidone in 30 ml of absolute methylene chloride was added within 15 minutes. After another 20 minutes 30 ml of 2N sulfuric acid were added, the organic phase was separated, dried and evaporated in vacuo at a bath temperature of a maximum of 30° C.

For the purification the aldehyde was filtered by silica gel (CHCl$_3$/C$_2$H$_5$OH = 9.5 : 0.5).

Rf = 0,62 (CHCl$_3$/C$_2$H$_5$OH= 9,5 : 0,5); IR(CH$_2$Cl$_2$)$\nu$= 1740 (CHO,COOCH$_3$); 1680 (C=O) cm$^{-1}$ $^1$H-NMR(CDCl$_3$)$\delta$=9,7 ppm (CHO)

9.1:
1-n-Butyl-[6'-carbomethoxy-(Z)-2'-hexene-yl(1')]-4-formyl-pyrrolidone in analogy to Example (9)
IR (CH$_2$Cl$_2$)$\nu$ = 1740 (CHO,COOCH$_3$); 1680 (C=O) cm$^{-1}$ $^1$H-NMR(CDCl$_3$):$\delta$= 9,7 ppm (CHO)

9.2:
1-Methyl-3-[6'-carbomethoxy-(Z)-3'-hexene-yl(1')]-4-formyl-pyrrolidone in analogy to Example (9)
Rf = 0.62 (CHCl$_3$/C$_2$H$_5$OH = 9,5 : 0,5); IR (CH$_2$Cl$_2$):$\nu$ = 1740 (CHO,COOCH$_3$); 1680 (C=O) cm$^{-1}$ $^1$H-NMR(CDCl$_3$):$\delta$=9,7 ppm (CHO)

10.
1-Methyl-3-[6'-carbomethoxy-(Z)-2'-hexene-yl(1')]-4-[3''-oxo-(E)-1''-octen-yl(1'')] (XIII)

To a suspension of 0.35 g (15 mmols) of sodium hydride in 70 ml of absolute dimethoxy ethane, a solution of 2.90 g (13 mmols) of dimethyl-2-oxoheptyl-phosphonate in 30 ml of absolute dimethoxy ethane was added dropwise at room temperature. After stirring for 1.5 hours at 20° C, 3.3 g (13 m/mols) of 1-methyl-3-[6'-carbomethoxy-(Z)-2'-hexene-yl(1')] -4-formyl-pyrrolidone were added dropwise. Stirring was continued for 1.5 hours at 25°, the whole was acidified with 2N sulfuric acid (p$_H$6), the solution was concentrated in vacuo, the residue was taken up in methylene chloride, the methylene chloride phase was dried with Na$_2$SO$_4$ and concentrated. From the remaining residue the dimethyl-2-oxoheptyl-phosphonate present was distilled off in high vacuum. The compound desired remained. It was freed from slight contaminations by column chromatography (silica gel; CHCl$_3$: C$_2$H$_5$OH = 9.5: 0.50).

Rf = 0.53 (ethyl acetate); IR (CHCl$_3$):$\nu$ = 1690 (C=O), 1740 (C=O); 1640 (C=C) cm$^{-1}$ 10.1: 1-Methyl-3-[6'-carbonmethoxy-(Z)-2-hexene-(3')-yl(1')]-4-[3''-oxo-(E)-1-octen-yl(1'')]-pyrrolidone in an analogy to Example(10)
Rf = 0,53 (Ethyl acetate); IR (CHCl$_3$):$\nu$ = 1690 (C=O), 1740 (C=O); 1640 (C=C)cm$^{-1}$

10.2:
1-Butyl-3-[6'-carbomethoxy-(Z)-2-hexene-(2')-yl(1')]-4-[3''-oxo-(E)-1''-octen-yl(1'')]-pyrrolidone in analogy to Example (10)

Rf = 0,84 (Ethyl acetate); IR (CHCl$_3$):$\nu$ = 1690 (C=O), 1740 (C=O); 1640 (C=C) cm$^{-1}$ 1-Methyl-3[6'-carbomethoxy-(Z)-2'-hexene-yl(1')]-4-[3''-(RS)-hydroxy-(E)-1''-octen-yl(1'']-pyrrolidone(I)

To a solution of 1.0 g (2.75 mmols) of 1-methyl-3-[6'-carbomethoxy-(Z)-2'hexene-yl(1')-]-4-[3''-oxo-(E)-1''octenyl(1'')]-pyrrolidone in 25 ml of absolute dimethoxyethane, 15 ml of a 0.84 molar Zn(BH$_4$)$_2$-solution (12.5 m mmoles) were added dropwise at 0° C, and stirring was continued for 2.5 hours at room temperature. 5 ml of a 2N sulfuric acid were added (p$_H$5), stirring was continued for a short time and the whole was buffered with saturated sodium bicarbonate solution to p$_H$7. The filtered solution was concentrated in vacuo and the residue was extracted three times with 100 ml of methylene chloride in each case.

The organic phase was dried and concentrated in vacuo. The remaining oil (0.8 g) was purified with column chromatography (CHCl$_3$:C$_2$H$_5$OH= 9.5:0.5/silica gel).

Rf$_1$ = 0,59 Rf$_2$ = 0,65 (CHCl$_3$ : C$_2$H$_5$OH = 9,5 : 0.5) IR (CHCl$_3$):$\nu$ = 1680 (C=O), 1730 (C=O), 3450 (OH) cm$^{-1}$

1-Methyl-3-[6'-carbomethoxy-(Z)-3'-hexene-yl(1')-]-4-[3''-(RS)-hydroxy-(E)-1''-octen-yl(1'')-]-pyrrolidone in analogy to Example (11)

Rf$_1$ = 0,59 Rf$_2$= 0,65 (CHCl$_3$: C$_2$H$_5$OH = 9,5 : 0,5) IR (CHCl$_3$):$\nu$ = 1680 (C=O), 1730 (C=O), 3450 (OH) cm$^{-1}$ 1-n-Butyl-3-[6'-carbomethoxy-(Z)-2'-hexene-yl(1')]-4-[3''-(RS)-hydroxy-(E)-1''-octen-yl(1'')-pyrrolidone in analogy to Example (11)

IR (CHCl$_3$):$\nu$= 1680 (C=O), 1730 (C=O), 3450 (OH) cm$^{-1}$ Rf$_{1/2}$ = 0.72 (Ethyl acetate)

1-Methyl-3-[6'-carbohydroxy-(Z)-2'-hexene-yl(1')-]-4-[3''-(RS)-hydroxy-(E)-1''-octen-yl(1'')]-pyrrolidone 0.64 g (1.75 m moles) of 1-methyl-3-[6'-carbomethoxy-(Z)-2'-hexene-yl(1')]-4-]3''-(RS)-hydroxy-(E)-1''-octen-yl (1'')]-pyrrolidone were dissolved in a mixture of 2.5 ml of 1N NaOH, 5 ml of methanol and 5 ml of dimethoxy ethane and stirred for 5 hours at room temperature. The whole was acidified with concentrated hydrochloric acid (p$_H$ = 1), extracted five times with 50 ml of methylene chloride in each case, the organic phase was dried over sodium sulfate and concentrated. The compound desired was obtained as a colorless resin.

Rf$_1$ = 0,40; Rf$_2$ = 0,48 (CHCl$_3$ : C$_2$H$_5$OH=9:1) IR (CHCl$_3$):$\nu$= 1680 (C=O), 1715 (C=O), 3400 (OH) cm$^{-1}$ 1-n-Butyl-3-[6'-carbohydroxy-(Z)-2'-hexene-yl(1')-]-4-[3''-(RS)-hydroxy-(E)-1''-octen-yl(1'')]-pyrrolidone in analogy to example (14) IR (CHCl$_3$):$\nu$= 1680 (C=O), 1715 (C=O), 3400 (OH) cm$^{-1}$; Rf=0,49, (CHCl$_3$: CH$_3$OH) = 9 : 1

1-Methyl-3-[6'-carbohydroxy-(Z)-3'-hexene-yl(1')]-4-]3''-(RS)-hydroxy-(E)-1''-octen-yl(1'')-]-pyrrolidone in analogy to Example (14)

Rf$_1$ = 0.40; Rf$_2$ = 0.48 (CHCl$_3$: C$_2$H$_5$OH = 9 : 1) IR (CHCl$_3$)$\nu$= 1680 (C=O), 1715 (C=O), 3400 (OH) cm$^{-1}$

EXAMPLE 17

1-Methyl-3-[6-carbomethoxy-2-hexine-yl-(1)]-4-hydroxymethyl pyrrolidone 29.4 g (138 mmoles) of 1-methyl-4-(2-tetrahydropyranyloxymethyl)-pyrrolidone dissolved in 90 ml of diethyl ether were added over 20 minutes at −70° C with stirring to 150 mols of LiN(i-C$_3$H$_7$)$_2$ in 150 ml of diethyl ether. After continued stirring for 45 minutes the solution was filled in a dropping funnel which can be cooled (−35° to −40° C) and added dropwise, while stirring, during 60 minutes to a solution maintained at −70° C of 29.1 g (149 mmoles) of 1-bromo-6-chloro-hexine-(2) in 135 ml of ether. After continued stirring for 90 minutes the solution was slowly heated to room temperature, 75 ml of water were added dropwise, the organic phase was separated and the aqueous phase was extracted three times with each 50 ml of diethyl ether. The combined ether phases were washed three times with 40 ml of cold 1N sulfuric acid, once with 50 ml of saturated sodium hydrogen carbonate solution and once with 50 ml of water. After drying and concentrating in vacuo, the organic phase yielded 46.6 g of crude 1-methyl-3-[6-chloro-2 -hexine-yl-(1)]-4-(2-tetrahydropyranyl)-oxy-methyl)-pyrrolidone [R'$_F$: 0.42 (ethyl acetate)], which can be used without further purification for the next reaction step.

17.2: 7.5 g (153 mmols) of sodium cyanide were put into 90 ml of DMSO and heated to 80° C 46.6 g (142.5 mmoles) of crude 1-methyl-3-[6-chloro-2-hexine-yl-(1)-]-4-(2-tetrahydropyranyl-oxymethyl)-pyrrolidone, dissolved in 40 ml of DMSO were added dropwise, while stirring. The mixture was stirred for 3 – 6 hours at 80° C. The course of the reaction was observed in the thin layer chromatogram (ethyl acetate). After the reaction has been completed the mixture was cooled to 10° C, 200 ml of water were added and the mixture was extracted three times with 200 ml of diethyl ether. The combined ether phases were washed three times with saturated sodium chloride solution and dried. After concentration in vacuo, 43.7 g of crude 1-methyl3-[6-cyano-2-hexine-yl-(1)]-4-(2-tetrahydropyranyl-oxymethyl)-pyrrolidone [R$_F$: 0.39 (ethyl acetate)] were obtained which can be used without further purification for the next reaction.

17.3: 11 g (0.275 mol) of sodium hydroxide were dissolved in 33 ml of water, 43.7 g (137.5 mmols) of 1-methyl-3-[6-cyano-2-hexine-yl-(1)]-4-(2-tetrahydropyranyl-oxymethyl)-pyrrolidone dissolved in 135 ml of ethyl alcohol, were added and the mixture was boiled under reflux for 18 hours. Then, the alcohol was distilled off in vacuo, 150 ml of icecold 2N sulfuric acid were added to the residue with icecooling and the mixture was extracted ten times with 100 ml of diethyl ether. After drying and concentrating the combined ether phases, 47.4 g of crude 1-methyl-3-[6-carbohydroxy-2-hexine-yl-(1)]-4-(2-tetrahydropyranyl-oxymethyl)-pyrrolidone were combined which were taken up directly in 250 ml of methylene chloride and to which 380 ml of a 0.5 molar ethereal diazomethane solution was added at 0° C. The mixture was allowed to stand for 30 minutes at 0° C and for 1 hour at room temperature. After concentration in vacuo, 43.7 of crude 1-methyl-3[6-carbomethoxy-2-hexine-yl-(1)]-4-(2-tetrahydropyranol-oxymethyl-pyrrolidone [R$_F$: 0.45 (ethyl acetate)] were obtained.

17.4: This product was dissolved in 200 ml of methanol, three drops of concentrated hydrochloric acid were added and the mixture was boiled under reflux for 75 minutes. After concentration in vacuo the remaining oil was purified by means of column chromatography [silica gel/ethyl acetate (for the separation of the by-products), then ethyl acetate :ethanol = 10:1.5]. 25 g of 1-methyl-3-[6-carbomethoxy-2-hexine-yl(1)-]-4-hydroxy-methyl-pyrrolidone

[R$_F$: 0.14 (ethyl acetate)] were obtained. n$_D^{20}$ = 1.5005 IR (CH$_2$Cl$_2$): $\nu$ = 3450 (OH), 1740 (C=O), 1690 (C=O) cm$^{-1}$ NMR-spectrum, solvent: CDCl$_3$ N—CH$_3$: 2.82 ppm; O—CH$_3$: 3.64 ppm.

EXAMPLE 18

1-Isopropyl-3-[6-carbomethoxy-2-hexine-yl-(1)]-4-hydroxymethylpyrrolidone

This compound was obtained in analogy to Example 17 starting from 1-isopropyl-4-(tetrahydropyranyl-oxymethyl)-pyrrolidone.

$n_D^{20} = 1.4945$

NMR spectrum, solvent: CDCl₃; O-CH₃: 3.63 ppm

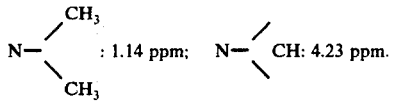

EXAMPLE 19

1-n-Butyl-3-[6-carbomethoxy-2-hexine-yl-(1)]-4-hydroxmethylpyrrolidone.

This compound was obtained in analogy to Example 17 starting from 1-n-butyl-4-(tetrahydropyranyl-oxymethyl)-pyrrolidone.

$n_D^{20} = 1.4855$

NMR spectrum, solvent: CDCl₃; O-CH₃: 3.61 ppm; N⁀⁀⁀CH₃: 0.9 ppm.

EXAMPLE 20

1-Methyl-3-[6-carbomethoxy-2-hexine-yl-(1)]-4-hydroxymethylpyrrolidone 29.1 g (91.5 mmols) of 1-methyl-3-[6-cyano-2-hexine-yl-(1)]-4-(2-tetrahydropyranyl-oxymethyl)-pyrrolidone were dissolved in 175 ml of diethyl ether and 90 ml of absolute methanol, the solution was saturated at 0° to −5° C with gaseous hydrogen chloride and it was stirred for about 2 - 3 hours at that temperature.

The thin layer chromatogram (silica gel, HCCl₃:CH₃OH = 90:10) showed that the tetrahydropyranyl radical was split off in a few minutes and the nitrile was completely transformed in the course of 2 to 3 hours into the imido-ether hydrochloride. Then, the excess hydrogen and the solvent were eliminated at 0 - 20° C in vacuo. The residue was taken up in 150 ml of methanol and the solution was adjusted to pH 1.5 - 2 with 33% strength aqueous sodium hydroxide solution with ice-cooling. To complete the hydrolysis of the imidoether-hydrochloride the solution was boiled under reflux for 50 - 60 minutes. For working up, the methanol was distilled off in vacuo, 50 ml of water was added to the residue and the ester formed was extracted with methylene chloride. The purification was carried out as in Example 17 with column chromatography.

19.1 g of 1-methyl-3-[6-carbomethoxy-2-hexine-yl-(1)]-4-hydroxymethyl-pyrrolidone were obtained.

The substance is identical with that obtained according to Example 1.

EXAMPLE 21

1-Methyl-3-[6-carbomethoxy-(Z)-2-hexene-yl-(1)]-4-hydroxymethyl-pyrrolidone 2.7 g (10 mmols) of 1-methyl-3-[6-carbomethoxy-2-hexine-yl-(1)]-4-hydroxymethyl pyrrolidone were dissolved in 20 ml of benzene to which solution 100 mg of Pd/CaCO₃ (10% Pd) and 1 ml of quinoline were added. Hydrogen was led in at 24° - 26° C while stirring thoroughly. After about 50 - 60 minutes 228 ml were consumed and the reaction came to a stop. For working up, the catalyst was suction-filtered, washed with benzene and the filtrate was concentrated in vacuo. The residue obtained was 2.3 g of 1-methyl-3-[6-carbomethoxy-(Z)-2-hexene-yl-(1)]-4-hydroxymethyl-pyrrolidone.

$R_F$: 0.15 (ethyl acetate)

$n_D^{20}$: 1.5004

IR(CH₂Cl₂): $\nu$ = 3450 (OH), 1740 (C=O), 1680 (C=O) cm⁻¹.

EXAMPLE 22

1-Butyl-3-[6-carbomethoxy-(Z)-2-hexene-yl-(1)]-4-hydroxymethyl-pyrrolidone

This compound was obtained in analogy in Example 21 starting from 1-butyl-3-[6-carbomethoxy-2-hexine-yl-(1)]-4-hydroxymethyl-pyrrolidone.

$R_F$: 0.43 (ethyl acetat)

IR(CH₂Cl₂): $\nu$ = 3450 (OH), 1740 (C=O), 1680 (C=O) cm⁻¹.

EXAMPLE 23

1-Isopropyl-3-[6-carbomethoxy-(Z)-2-hexene-yl-(1)]-4-hydroxymethyl-pyrrolidone

This compound was obtained in analogy to Example 21 starting from 1-isopropyl-3-[6-carbomethoxy-2-hexine-yl-(1)]-4-hydroxymethyl-pyrrolidone.

$R_F$: 0.34 (ethyl acetate)

IF(CH₂Cl₂): $\nu$ = 3450 (OH), 1740 (C=O), 1680 (C=O) cm⁻¹.

According to the same process especially the following compounds of the formula I may be prepared. In this way not only the esters but also the acids and the physiologically tolerable amine and metal salts thereof can be prepared.

24: 1-Methyl-3-[6′-carbomethoxy-(Z)-2′-hexen-yl(1′)]-4-[3″-(RS)-hydroxy-(E)-1″-decen-yl(1″)]-pyrrolidone
25: 1-Methyl-3-[6′-carbomethoxy-(Z)-2′-hexen-yl(1′)]-4-[3″-(RS)-hydroxy-(E)-1″nonen-yl(1″)]-pyrrolidone
26: 1-Methyl-3-[6′-carbomethoxy-(Z)-2′-hexen-yl(1′)]-4-[3″-(RS)-hydroxy-(E)-1″-hexene-yl (1″)]-pyrrolidone
27: 1-Methyl-3-[6′-carbomethoxy-(Z)-2′-hexen-yl(1′)]-4-[3″-(RS)-hydroxy-4″, 4″-dimethyl-(E)-1″-octene-yl(1″)]-pyrrolidone
28: 1-Methyl-3-[6′-carbomethoxy-(Z)-2′-hexen-yl(1′)]-4-[3″-(RS)-hydroxy-3″-cyclohexyl-(E)-1″-propene-yl-(1″)]-pyrrolidone
29: 1-Methyl-3-[6′-carbomethoxy-(Z)-2′-hexen-yl(1′)]-4-[3″-(RS)-hydroxy-3″-cycloheptyl-(E)-1″-propene-yl(1″)]-pyrrolidone
30: 1-Methyl-3-[6′-carbomethoxy-(Z)-2′-hexen-yl(1′)]-4-[[3″-(RS)-hydroxy-4″-methyl-4-[p-(p-chlorophenoxy)-phenoxy]-(E)-1′″-buten-yl(1″)]]-pyrrolidone
31 1-Methyl-3-[6′-carbomethoxy-(Z)-2′-hexen-yl(1′)]-4-[[3″-(RS)-hydroxy-4″,4″-dimethyl-4-[p-(p-chlorophenoxy)-phenoxy]-(E)-1″-buten-yl(1″)]]-pyrrolidone
32: 1-Methyl-3-[6′-carbomethoxy-(Z)-2′-hexen-yl(1′)]-4-[3″-(RS)-hydroxy-5″-ethylthio-(E)-1″-pentene-1″-(yl)]-pyrrolidone
33: 1-Methyl-3-[6′-carbomethoxy-(Z)-2′-hexen-yl(1′)]-4-[3″-(RS)-hydroxy-4″-p-fluorophenoxy-(E)-1′″butene-1″-(yl)]-pyrrolidone
34: 1-Methyl-3-[6′-carbomethoxy-(Z)-2′-hexen-yl(1′)]-4-[3″-(RS)-hydroxy-4″-p-chlorophenoxy-(E)-1″-butene-1″(yl)]-pyrrolidone
33: 1-Methyl-3-[6′-carbomethoxy-(Z)-2′-hexen-yl(1′)]-4-[3″-(RS)-hydroxy-4″-meta-trifluoromethylphenoxy-(E)-1″-butene-1″(yl)]-pyrrolidone 36: 1-Methyl-3-[6'-carbomethoxy-(Z)-2'-hexen-yl(1')]-4-[3''-(RS)-hydroxy-4''-(methyl-propionyl-amino)-(E)-1''-butene-1'''(yl)]-pyrrolidone 1-Methyl-3-[6'-carbomethoxy-(Z)-3'-hexen-yl(1')]-4-[3''-(RS)-hydroxy-(E)-1''-decen-yl(1'')]-pyrrolidone 38 1-Methyl-3-[6'-carbomethoxy-(Z)-3'-hexen-yl(1')]-4-[3''-(RS)-hydroxy-(E)-1''-nonen-yl(1'')]-pyrrolidone 39: 1-Methyl-3-[6'-carbomethoxy-(Z)-3''-hexen-yl(1')]-4-[3''-(RS)-hydroxy-(E)-1''-hexen-yl(1'')]-pyrrolidone 40: 1-Methyl-3-[6-carbomethoxy-(Z)-3'-hexen-yl(1')]-4-[3''-(RS)-hydroxy-4'', 4''-dimethyl-(E)-1''-octene-yl(1'')]-pyrrolidone 41: 1-Methyl-3-[6'-carbomethoxy-(Z) -3'-hexen-yl(1')]-4-[3''-(RS)-hydroxy-3''-cyclohexyl-(E)-1''-propene-yl(1'')]-pyrrolidone 42: 1-Methyl-3-[6'-carbomethoxy-(Z)-3'-hexen-yl(1')]-4[3''-(RS)-hydroxy-3''-cycloheptyl-(E)-1''-propene-yl(1'')]-pyrrolidone 43: 1-Methyl-3-[6'-carbomethoxy-(Z)-3'-hexen-yl(1')]-4[3''-(RS)-hydroxy-4''-methyl-4-[p-(chlorophenoxy)-phenoxy]-(E)-1''-buten-yl(1'')]-pyrrolidone 44: 1-Methyl-3-[6'-carbomethoxy-(Z)-3'-hexen-yl(1')]-4-[3''-(RS)-hydroxy-4'', 4''-dimethyl-4-[p-(p-chlorophenoxy)-phenoxy](E)-1''-buten yl(1'')]-pyrrolidone 45: 1-Methyl-3-[6'-carbomethoxy-(Z)-3'-hexen-yl(1')]-4-[3''-(RS)-hydroxy-5''-ethylthio-(E)-1''-pentene-1'''(yl)]-pyrrolidone 46: 1-Methyl-3-[6'-carbomethoxy-(Z)-3'-hexen-yl(1')]-4-[3''-(RS)-hydroxy-4''-p-fluorophenoxy-(E)-1'''-buten-1'''(yl)]-pyrrolidone 47: 1-Methyl-3-[6'-carbomethoxy-(Z)-3'-hexen-yl(1')]-4-[3''-(RS)-hydroxy-4''-p-chlorophenoxy-(E)-1''-butene-1'''(yl)]-pyrrolidone 48: 1-Methyl-3-[6'-carbomethoxy-(Z)-3'-hexen-yl(1')]-4-[3''-(RS)-hydroxy-4''-meta-trifluoromethylphenoxy-(E)-1''-butene-1'''(yl)]-pyrrolidone 49: 1-Methyl-3-[6'-carbomethoxy-(Z)-3'-hexen-yl(1')]-4-[3''-(RS)-hydroxy-4''-(methyl-propionyl-amine)-(E)-buten-1'''(yl)]-pyrrolidone 50: 1-Butyl-3-[6'-carbomethoxy-(Z)-2-hexen-yl(1')]-4-[3''-(RS)-hydroxy-(E)-1''-decen-yl(1'')]-pyrrolidone 51: 1-Butyl-3-[6'-carbomethoxy-(Z)-2'-hexen-yl(1')]-4-[3''-(RS)-hydroxy-(E)-1''-nonen-yl(1'')]-pyrrolidone 52: 1-Butyl-3-[6'-carbomethoxy-(Z)-2'-hexen-yl(1')]-4-[3''-(RS)-hydroxy-(E)-1''-hexen-yl(1'')]-pyrrolidone 53: 1-Butyl-3-[6'-carbomethoxy-(Z)-2'-hexen-yl(1')]-4-[3''-(RS)-hydroxy-4'',4''-dimethyl-(E)-1''-octen-yl(1'')]-pyrrolidone 54: 1-Butyl-3-[6'-carbomethoxy-(Z)-2'-hexen-yl(1')]-4-[3''-(RS)-hydroxy-4'',4''-dimethyl-5''-ethoxy-(E)-1''-penten-yl(1'')]-pyrrolidone 55: 1-Butyl-3-[6'-carbomethoxy-(Z)-2'-hexen-yl(1')]-4-[3''-(RS)-hydroxy-3''-cyclohexyl-(E)-1''-propen-yl(1'')]-pyrrolidone 56: 1-Butyl-3-[6'-carbomethoxy-(Z)-2'-hexen-yl(1')]-4-[3''-(RS)-hydroxy-3''-cycloheptyl-(E)-1''-propen-yl(1'')]-pyrrolidone 57: 1-Butyl-3-[6'-carbomethoxy-(Z)-2'-hexen-yl(1')]-4-[[3''-(RS)-hydroxy-4''-methyl-4''-[p-(p-chlorophenoxy)-phenoxy]-(E)-1''-buten-yl(1'')]]-pyrrolidone 58: 1-Butyl-3-[6'-carbomethoxy-(Z)-2'-hexen-yl(1')]-4-[[3''-(RS)-hydroxy-4'',4''-dimethyl-4''-[p-(p-chlorophenoxy)-phenoxy]-(E)-1''-buten-yl(1'')]]-pyrrolidone 59: 1-Butyl-3-[6'-carbomethoxy-(Z)-2'-hexen-yl(1')]-4-[3''-(RS)-hydroxy-5''-ethylthio-(E)-1'''-penten-yl(1'')]-pyrrolidone 60: 1-Butyl-3-[6'-carbomethoxy-(Z)-2'-hexen-yl(1')]-4-[3''-(RS)-hydroxy-4''-(methyl-propionyl-amino)-(E)-1''-buten-yl(1'')]-pyrrolidone 61: 1-Butyl-3-[6'-carbomethoxy-(Z)-2'-hexen-yl(1')]-4-[3''-(RS)-hydroxy-4''-(p-fluorophenoxy)-(E)-1''-buten-yl(1'')]-pyrrolidone 62: 1-Butyl-3-[6'-carbomethoxy-(Z)-2'-hexen-yl(1')]-4-[3''-(RS)-hydroxy-4''-(p-chlorophenoxy)-(E)-1'-buten-yl(1'))-pyrrolidone 63: 1-Butyl-3-[6'-carbomethoxy-(Z)-2'-hexen-yl(1')]-4-[3''-(RS)-hydroxy-4''-(m-trifluoromethylphenoxy)-(E)-1''-buten-yl(1'')]-pyrrolidone 64: 1-Methyl-3-[6'-carbomethoxy-(Z)-2'-hexen-yl(1')]-4-[3''-(RS)-hydroxy-4'',4''-dimethyl-5''-ethoxy-(E)-1''-penten-yl(1'')]-pyrrolidone 65: 1-Methyl-3-[6'-carbomethoxy-(Z)-3'-hexen-yl(1')]-4-[3''-(RS)-hydroxy-4'',4''-dimethyl-5-ethoxy-(E)-1''-penten-yl(1'')]-pyrrolidone 66: 1-Methyl-3-[6'-carbomethoxy-(Z)-2'-hexen-yl(1')]-4-[3''-(RS)-hydroxy-4'',4''-dimethyl-5''-methoxy-(E)-1''-penten-yl(1'')]-pyrrolidone 67: 1-Butyl-3-[6'-ocarbomethoxy-(Z)-2'-hexen-yl(1')]-4-[3''-(RS)-hydroxy-4'',4''-dimethyl-5''-methoxy-(E)-1''-penten-yl(1'')]-pyrrolidone 68: 1-Methyl-3-[6'-carbomethoxy-(Z)-2'-hexen-yl(1')]-4-[3''-(RS)-hydroxy-4'',4''-dimethyl-5''-allyloxy-(E)-1''-penten-yl(1'')]-pyrrolidone 69: 1-Butyl-3-[6'-carbomethoxy-(Z)-2'-hexen-yl(1')]-4-[3''-(RS)-hydroxy-4'',4''-dimethyl-5''-allyloxy-(E)-1''-penten-yl(1'')]-pyrrolidone 70: 1-Methyl-3-[6'-carbomethoxy-(Z)-2'-hexen-yl(1')]-4-[3''-(RS)-hydroxy-4'',4''-dimethyl-5''-isobutoxy-(E)-1''-penten-yl(1'')]-pyrrolidene 71: 1-Butyl-3-[6'-carbomethoxy-(Z)-2'-hexen-yl(1')]-4-[3''-(RS)-hydroxy-4'',4''-dimethyl-5''-isobutoxy-(E)-1''-penten-yl(1'')]-pyrroldidone 72: 1-Methyl-3-[7-carbomethoxy-(Z)-2'-hepten-yl(1')]-4-[3''-(RS)-hydroxy-4'',4''-dimethyl-5''-ethoxy-(E)-1''-penten-yl(1'')]-pyrrolidone 73: 1-n-Butyl-3-[7-carbomethoxy-(Z)-2'-hepten-yl(1')]-4[3''-(RS)-hydroxy-4'',4''-dimethyl-5''-allyloxy-(E)-1''-penten-yl(1'')]-pyrrolidone

What we claim is:

1. A pyrrolidone of the formula

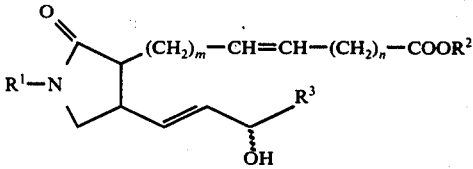

the corresponding free acid, or a physiologically compatible metal or amine salt thereof, wherein $R^1$ is straight-chain or branched alkyl having 1 to 6 carbon atoms; $R^2$ is straight-chain or branched alkyl having 1 to 4 carbon atoms; $R^3$ is straight-chain or branched alkyl having 1 to 10 carbon atoms; $m$ is 1 or 2; $n$ is 2 or 3; and wherein the side chains in the 3- and 4-positions in the pyrrolidone ring are in transposition to each other.

2. A compound as in claim 1 which is 1-methyl-3-[6'-carbomethoxy-(Z)-2'-hexene-yl (1')]-4-[3''-(RS)-hydroxy-(E)-1''-octene-yl (1'')]-pyrrolidone.

3. A compound as in claim 1 which is 1-methyl-3-[6'-carbohydroxy-(Z)-2'-hexene-yl (1')]-4-[3''-(RS)-hydroxy-(E)-1''-octene-yl (1'')]-pyrrolidone.

4. A compound as in claim 1 which is 1-butyl-3-[6'-carbomethoxy-(Z)-2'-hexene-yl(1')]-4-[3''-(RS)-hydroxy-(E)-1''-decene-yl(1'')]-pyrrolidone.

* * * * *